US011351158B2

(12) United States Patent
Dale et al.

(10) Patent No.: US 11,351,158 B2
(45) Date of Patent: *Jun. 7, 2022

(54) RIFABUTIN TREATMENT METHODS, USES, AND COMPOSITIONS

(71) Applicant: BIOVERSYS AG, Basel (CH)

(72) Inventors: Glenn E. Dale, Basel (CH); Sergio Lociuro, Basel (CH); Christian Kemmer, Riehen (CH); Vincent Trebosc, Rixheim (FR); Marc Gitzinger, Laufenburg (CH)

(73) Assignee: BIOVERSYS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/983,689

(22) Filed: Aug. 3, 2020

(65) Prior Publication Data

US 2021/0077471 A1    Mar. 18, 2021

Related U.S. Application Data

(60) Provisional application No. 62/977,659, filed on Feb. 17, 2020, provisional application No. 62/941,160, (Continued)

(51) Int. Cl.
*A61K 31/438*    (2006.01)
*A61P 31/04*    (2006.01)
(Continued)

(52) U.S. Cl.
CPC .......... *A61K 31/438* (2013.01); *A61K 9/0019* (2013.01); *A61K 9/0043* (2013.01);
(Continued)

(58) Field of Classification Search
CPC .................................................. A61K 31/438
See application file for complete search history.

(56) References Cited

U.S. PATENT DOCUMENTS 6,645,508 B1 * 11/2003 Chen .................... A61K 8/4913
424/400
2014/0341999 A1 * 11/2014 Ipatova .................. A61K 9/127
424/489
(Continued)

FOREIGN PATENT DOCUMENTS

CN      101362067 A  *  2/2009
WO      2012106364 A1    8/2012

OTHER PUBLICATIONS

Muller et al (Veterinary Medicine International, vol. 2010, Article ID 321797, 7 pgs) (Year: 2010).*
(Continued)

*Primary Examiner* — Benjamin J Packard
(74) *Attorney, Agent, or Firm* — Brown Rudnick LLP; Thomas C. Meyers

(57) ABSTRACT

The invention provides systems and methods for increased clinical efficacy of rifabutin against *A. baumannii*. The invention takes advantage of the discovery of a ferric-coprogen (FhuE) receptor that is responsible for the uptake of rifabutin into *A. baumannii* cells. Methods preferably include obtaining a sample from a patient suspected of having an infection; performing a test on the sample to identify an infection of *A. baumannii* in the patient; and providing a formulation of rifabutin for treating the patient that, when administered to the patient, maximizes a resultant AUC and/or $C_{max}$. The method may include administering the formulation of rifabutin to the patient. Preferably the formulation is delivered to the patient, e.g., by intravenous injection and results in a $C_{max}$ is that greater than about 2 mg/L and optionally less than about 50 mg/L.

21 Claims, 8 Drawing Sheets

Related U.S. Application Data filed on Nov. 27, 2019, provisional application No. 62/902,019, filed on Sep. 18, 2019, provisional application No. 62/899,257, filed on Sep. 12, 2019.

(51) Int. Cl.
  *A61K 9/00* (2006.01)
  *A61K 31/546* (2006.01)
  *A61K 38/12* (2006.01)

(52) U.S. Cl.
  CPC .......... *A61K 9/0053* (2013.01); *A61K 9/0073* (2013.01); *A61K 31/546* (2013.01); *A61K 38/12* (2013.01); *A61P 31/04* (2018.01)

(56) References Cited

U.S. PATENT DOCUMENTS

| | | |
|---|---|---|
| 2019/0269806 A1 | 9/2019 | Timmins et al. |
| 2020/0222373 A1 | 7/2020 | Spellberg et al. |

OTHER PUBLICATIONS

Of Telussa ("Reclaiming the Activity of Lost Therapeutics" (2016) Graduate Theses and Dissertations, http://scholarcommons.usf.edu/etd/6411, Univ Southern Florida). (Year: 2016).*

Cadieux, 2000, Sequence changes in the ton box region of BtuB affect its transport activities and interaction with TonB protein, J. Bacteriol., 182:5954-5961.

Funahashi, 2012, Identification and characterization of an outer membrane receptor gene in Acinetobacter baumannii required for utilization of desferricoprogen, rhodotorulic acid, and desferrioxamine B as xenosiderophores, Biol. Pharm. Bull., 35:753-760.

Giannouli, 2011, Molecular epidemiology and mechanisms of rifampicin resistance inisolates from Italy, International Journal of Antimicrobial Agents, vol. 36, No. 1, pp. 58-63.

Gumbo, 2007, Concentration-dependent *Mycobacterium tuberculosis* killing and prevention of resistance by rifampin, Antimicrobial Agents and Chemotherapy, 51(11):3781-3788.

Hafner, 1998, Tolerance and pharmacokinetic interactions of rifabutin and clarithromycin in human immunodeficiency virus-infected volunteers, Antimicrobial Agents Agents and Chemotherapy 42(3):631-639.

Hickman, 2017, Gating of TobB-dependent transporters by substrate-specific forced remodelling, Nat. Commun., 8:1-12.

Howard, 2012, Acinetobacter baumannii: An emerging opportunistic pathogen, Virulence 3(3):243-250.

International Seach Report and Written Opinion issued in International Application No. PCT/IB2020/000647, dated Nov. 2, 2020, 22 pages.

International Search Report and Written Opinion issued in International Application No. PC/IB2020/000645, dated Nov. 27, 2020, 22 pages.

Jenkins, 2012, Current Concepts in Laboratory Testing to Guide Antimicrobial Therapy, Mayo Clin. Proc., 87:290-308.

Luna, 2020, A nutrient-limited screen unmasks rifabutin hyperactivity for extensively drug-resistant, Nature Microbiology, Nature Publishing Group UK, London, vol. 5, No. 9, pp. 1134-1143.

MacNair, 2018, Overcoming mcr-1 mediated colistin resistance with colistin in combination with other antibiotics, Nature Communication, Vo. 9, No. 1, 8 pages.

Noinaj, 2010, TonB-dependent transporters: regulation, structure, and function, Annu. Rev. Microbiol., 64:43-60.

Nwugo, 2011, Deciphering the iron response in Acinetobacter baumannii: A proteomics approach, Journal of Proteomics, 74(1):44-58.

Office Action issued in U.S. Appl. No. 16/983,667, dated Oct. 7, 2020, 7 pages.

Peleg, 2008, Acinetobacter baumannii: Emergence of a successful pathogen, Clin Microbiol Rev, 21(3):538-582.

Rajamani, 2019, Robust biofilm assay for quantification and high throughput screening applications, Journal of Microbiological Methods, vol. 159:179-185.

Saisho, 2018. Pharmacokinetics, Safety, and Tolerability of Cefiderocol, a Novel Siderophore Cephalosporin for Gram-Negative Bacteria, in Healthy Subjects, Antimicrobial Agents and Chemotherapy, vol. 62, No. 3, 2 pages.

Sauer, 1987, Ferriccoprogen receptor FhuE of *Escherichia coli*: Processing and sequence common to all TonB-dependent outer membrane receptor proteins, J Bact 169(5):2044-2049.

Sun, 2016, Rapid antimicrobial susceptibility test for identification of new therapeutics and drug combinations against multidrug-resistant bacteria, Emerging Microbes & Infections, vol. 5, No. 1, pp. 1-11.

Wong, 2017, Clinical and Pathophysiological Overview of Acinetobacter Infections: a Century of Challenges, Clinical Microbiology Review, vol. 30, No. 1, pp. 409-447.

Yu, 2018, Novel partners with colistin to increase its in vivo therapeutic effectiveness and prevent the occurrence of colistin resistance in NDM- and MCR-co-producing *Escherichia coli* in a murine infection model, Journal of Antimicrobial Chemotherapy, col. 74, pp. 87-95.

* cited by examiner

RIFABUTIN TREATMENT METHODS, USES, AND COMPOSITIONS

RELATED APPLICATIONS

This application claims the benefit of and priority to U.S. Provisional Patent Application Ser. Nos. 62/902,019, filed Sep. 18, 2019, 62/899,257, filed Sep. 12, 2019, 62/941,160, filed Nov. 27, 2019, and 62/977,659, filed Feb. 17, 2020, the content of each of which is incorporated herein in its entirety.

TECHNICAL FIELD

The present invention discloses compositions and methods for the activation of the *A. baumannii* ferric-coprogen (FhuE) receptor and the use of high systemic exposures of rifabutin ($C_{max}$ and AUC) that are effective for treating *A. baumannii* infection.

BACKGROUND

Bacterial infections are often difficult to treat due to the emergence of multi-drug resistant (MDR) or extensively-drug resistant (XDR) strains of bacteria. Of particular concern, according to the World Health Organization's priority list, are carbapenem and third generation cephalosporin-resistant *Acinetobacter baumannii*, *Pseudomonas aeruginosa* and *Enterobacteriaceae* spp., belonging to the antimicrobial resistant Gram-negative pathogens known by the acronym 'ESKAPE'.

Patients suffering from antimicrobial resistant infection are usually too ill to take oral formulations of 'last resort' antibiotics, so intravenous (IV) administration is the only method of delivery sufficient to provide antibiotic treatment. Unfortunately, most antibiotics have not been formulated for IV administration because they are difficult or impossible to formulate into soluble forms.

Rifabutin (also known as LM 427 and Mycobutin®) is a spiro-piperidyl-rifamycin derived from rifamycin-S. Mycobutin® was approved by FDA as an oral formulation in 1992. Mycobutin® (150 mg capsules) capsules are indicated for the prevention of disseminated *Mycobacterium avium* complex (MAC) disease in patients with advanced HIV infection. Rifabutin is widely known to have low outer membrane permeability against Gram-negative pathogens, thus limiting its cellular uptake into those life-threatening ESKAPE pathogens. As such, formulations or alternative routes of administration of rifabutin have not been fully explored, a situation that is compounded by its poor solubility.

In closely-related rifamycin molecules, such as rifampin (also known as rifampicin), microbial killing of *Mycobacterium tuberculosis* is linked to the area under the concentration-time curve-to-MIC ratio (AUC/MIC) whereas the suppression of resistance was associated with the free peak concentration ($C_{max}$)-to-MIC ratio ($C_{max}$/MIC) and not the duration that the rifampin concentration was above MIC. Moreover, the post-antibiotic effect duration was also most closely related to the $C_{max}$/MIC ratio (see Gumbo, 2007, Concentration-dependent *Mycobacterium tuberculosis* killing and prevention of resistance by rifampin, Antimicrobial Agents and Chemotherapy, 51(11):3781-3788, incorporated by reference). Thus, to achieve a microbial killing and to prevent the emergence of resistance in the clinical arena high plasma concentrations of drug are required.

In healthy adult volunteers a nominal therapeutic oral dose of 300 mg rifabutin produces a mean $C_{max}$ of 0.375 mg/L which is attained at approximately 3 hours after oral administration (rifabutin product monograph). The PK of rifabutin is linear after single administration of 300, 450 and 600 mg PO to healthy volunteers with a $C_{max}$ in the range of 0.4 to 0.7 mg/L (rifabutin product monograph). In a study in HIV infected patients receiving the recommended daily dose of rifabutin (300 mg/day) the plasma concentrations at steady state were $C_{max}$ was 0.59±0.33 mg/L and the AUC was 8.6±8.2 mg*h/L (Hafner, 1998, Tolerance and pharmacokinetic interactions of rifabutin and clarithromycin in human immunodeficiency virus-infected volunteers, Antimicrobial Agents and Chemotherapy 42(3):631-639, incorporated by reference).

Since rifabutin is approximately 90% protein bound the free drug concentrations after oral administration are very low. In healthy adult volunteers at least 53% of the oral dose is absorbed whereas the absolute bioavailability assessed in HIV positive patients in a multiple dose study was 20% on day 1 and 12% on day 28. The low systemic exposure ($C_{max}$ and AUC) of rifabutin after oral dosing limits the utility of rifabutin for the treatment of serious infections such as those caused by the ESKAPE pathogen *Acinetobacter baumannii* (*Acinetobacter calcoaceticus-baumannii* complex). Moreover, the oral administration of rifabutin to patients with such infections will likely lead to rapid development of resistance.

SUMMARY

The invention provides systems and methods for increased clinical efficacy of rifabutin against *A. baumannii*. The discovery by the inventors of a novel mechanism of action has resulted in the ability of rifabutin to maintain significant activity against *A. baumannii*, while having only minimal activity against other Gram-negative pathogens. The invention takes advantage of the discovery of a ferric-coprogen (FhuE) receptor that is responsible for the uptake of rifabutin, but not of the closely related drug rifampin, into *A. baumannii* cells. In one aspect, the invention provides high AUC and $C_{max}$ of administered rifabutin, which allow for increased clinical efficacy via activation of the FhuE receptor and, at the same time, reducing the likelihood of resistance—a significant problem in standard oral formulations of rifabutin and related drugs. The inventors discovered that high exposures and in particular $C_{max}$ cannot be achieved by the currently available oral route of administration but can be achieved by intravenous injection or by methods known in the art for modified oral released or by inhalation if locally high $C_{max}$ and AUC are required.

In certain embodiments, rifabutin liquid formulations are provided for intravenous (IV) administration, the formulations being effective against *Acinetobacter baumannii*. Rifabutin liquid formulations may exploit siderophores that modulate a ferric-coprogen (FhuE) receptor in bacterial cell membranes to transport rifabutin across bacteria cells membranes. This provides an unexpected clinical advantage previously unknown for oral rifabutin. Formulations of rifabutin disclosed herein are useful for treating bacterial infections where oral administration of an antimicrobial is impractical or impossible. The formulations and methods of the present invention provide the medical community with novel treatments for patients incapacitated by life-threatening bacterial infections.

In certain embodiments, rifabutin uses the presence of siderophores that modulate TonB-dependent siderophore receptors in bacteria cells. The TonB-dependent siderophore receptors may be ferric-coprogen (FhuE) receptors. A preferred siderophore is one that modulates a bacterial TonB-dependent siderophore receptor. For example, a preferred siderophore may be any iron chelator that mediates a TonB-dependent siderophore receptor's uptake of rifabutin. For example, the siderophore may be an apotransferrin or may be a transferrin. The siderophore may be loaded with an iron complex. The siderophore that is iron-loaded may be a transferrin.

Rifabutin may use the presence of siderophores to modulate a TonB-dependent siderophore receptor of *Acinetobacter baumannii*.

As noted, methods of the invention are based on the recognition that FhuE receptor activation allow entry of rifabutin in *A. baumannii* and, in addition, that high $C_{max}$ and AUC of rifabutin can be achieved in patients for effective treatment of infections caused by this pathogen and for reducing likelihood of resistance development. A preferred rifabutin formulation comprises rifabutin powder in water, a solvent, and an acid to promote dissolution of the rifabutin. The solvent may be present in a concentration from about 25% to about 75%, from about 30% to about 70%, from about 35% to about 65%, from about 40% to about 60%, from about 45% to about 55%, from about 45% to about 65%, from about 50% to about 65%, from about 50% to about 60%, from about 50% to about 55%, or about 50%. Preferably, the solvent and the distilled water are in a 1:1 ratio. Preferred solvents include polyoxyethylene sorbitan monooleate (Tween 80), sorbitan monooleate polyoxyethylene sorbitan monolaurate (Tween 20), polyethylene glycol (PEG), propylene glycol, N-methyl-2-pyrrolidone (NMP), glycerin, ethanol, dimethylacetamide (DMA), diethylene glycol monoethyl ether (transcutol HP), or dimethyl isosorbide (DMI). In preferred embodiments, the solvent is DMI. A reconstituted solution of the invention preferably contains about 250 mg/ml (1:1 solvent/water) or about 166.7 mg/m. (2:1 solvent/water), however concentrations of the reconstituted solution may be as high as about 300 mg/ml. In certain embodiments, a more dilute solution is required and that is obtained by adding more water to the solvent. For example, rifabutin in a 1:4 solvent/water ratio will result in a solution of about 50 mg/ml. Such formulations are useful for treating a variety of conditions caused by *A. baumannii*, such as, but not limited to, bacteremia, Ventilator-Associated Bacterial Pneumonia (VABP), Hospital-Acquired Bacterial Pneumonia (HABP) and Urinary Tract Infections (UTI).

According to the present invention, rifabutin has potent activity towards *A. baumannii* due to exploitation of the *A. baumannii* ferric-coprogen (FhuE) receptor. Moreover, the invention provides methods for determining susceptibility of *A. baumannii* isolates to rifabutin treatment.

According to the invention, disclosed intravenous formulations achieve critical $C_{max}$ and AUC that cannot be achieved using currently available oral formulations. This provides an unexpected clinical advantage previously unavailable for rifabutin. The intravenous administration of rifabutin provides a novel treatment for patients with life-threatening bacterial infections such as those caused by *Acinetobacter baumannii*.

Formulations of the invention include an acid. The solvent solution may also include an acid. The acid may be added to the solvent solution to form a reconstitution solvent. The acid may be in a concentration sufficient to cause dissolution of rifabutin when adding rifabutin to the reconstitution solvent. The acid may be in a concentration from about 1.0% to about 5.0%, from about 1.1% to about 4.9%, from about 1.2% to about 4.8%, from about 1.3% to about 4.7%, from about 1.4% to about 4.6%, from about 1.5% to about 4.5%, from about 1.6% to about 4.4%, from about 1.7% to about 4.3%, from about 1.8% to about 4.2%, from about 1.9% to about 4.1%, from about 2.0% to about 4.0%, from about 2.1% to about 3.9%, from about 2.2% to about 3.8%, from about 2.3% to about 3.7%, from about 2.4% to about 3.6%, from about 2.5% to about 3.5%, from about 2.5% to about 3.4%, from about 2.5% to about 3.3%, from about 2.5% to about 3.2%, from about 2.5% to about 3.1%, from about 2.5% to about 3.0%, from about 2.5% to about 2.9%, from about 2.5% to about 2.8%, from about 2.5% to about 2.7%, or from about 2.5% to about 2.6%. The acid may be hydrochloric, methanesulfonic, phosphoric, 1-tartaric, d-glucuronic, 1-malic, d-gluconic, 1-lactic, acetic or 1-aspartic. Preferably, the acid is acetic acid.

The formulation containing an acid has a pH from about 3.0 to about 10.0, from about 3.0 to about 9.0, from about 3.0 to about 8.0 from about 3.0 to about 7.0, from about 3.0 to about 6.0, from about 4.0 to about 10.0, from about 4.0 to about 9.0, from about 4.0 to about 8.0 from about 4.0 to about 7.0, from about 4.0 to about 6.0, from about 5.0 to about 6.0, from about 5.1 to about 5.9, from about 5.2 to about 5.8, from about 5.3 to about 5.7, from about 5.4 to about 5.6, from about 5.5 to about 5.6, from about 5.5 to about 5.7, from about 5.5 to about 5.8, from about 5.5 to about 5.9, or a pH of ≥4.5. Preferably, the pH is from about 5.0 to about 6.0.

An intravenous rifabutin formulation may be manufactured by a process comprising preparing a solution comprising a solvent and distilled water in a 1:1 ratio in the presence of an acid suitable to promote dissolution of said rifabutin. Rifabutin may be present in a solid form or a powder form that is soluble in a liquid medium. Rifabutin may be dissolved in a solvent. Rifabutin may be soluble in an aqueous solution of 50% solvent (i.e., 1:1 solvent-distilled water) in the presence of an acid.

As such, rifabutin may be dissolved in a reconstitution solution containing an acid in an aqueous solution of a solvent in distilled water. Rifabutin may be added to the reconstitution solvent in an amount sufficient to produce a final solution having rifabutin in a concentration from about 150 mg/mL to about 350 mg/mL, from about 160 mg/mL to about 325 mg/mL, from about 170 mg/mL to about 300 mg/mL, from about 180 mg/mL to about 275 mg/mL, from about 190 mg/mL to about 265 mg/mL, from about 200 mg/mL to about 255 mg/mL, from about 210 mg/mL to about 250, mg/mL, from about 225 mg/mL to about 255 mg/mL, from about 235 mg/mL to about 255 mg/mL, from about 245 mg/mL to about 255, mg/mL, or from about 250 mg/mL to about 255 mg/mL. Preferably, the rifabutin solution or salt solution thereof contains about 250 mg/mL rifabutin. Adding the rifabutin to the reconstitution solution forms a reconstituted solution of rifabutin. The reconstituted rifabutin solution or salt solution thereof may be a concentrated solution not yet ready for parenteral administration. The concentrated solution may be a sterile solution.

The rifabutin solutions of the present invention may be in the form of a formulation for parenteral administration. The reconstituted rifabutin solutions may be diluted with a pharmaceutically accepted diluent for intravenous administration of a therapeutically effective dose of rifabutin. For example, the reconstituted rifabutin solution may be added to a pharmaceutically accepted diluent to prepare it for sterilized injection into a subject. The diluent may be a sodium chloride solution.

Formulations may include a solvent. In various embodiments, the w/v ratio of rifabutin to solvent may be from about 4:1 to about 1:4, from about 2:1 to about 1:3, or from about 1:1 to about 1:2. The w/v ratio of rifabutin to solvent may be about 4:1, about 3:1, about 2:1, about 1:1, about 1:2, about 1:3, or about 1:4.

In certain embodiments, the formulation may be provided to achieve systemic concentrations of rifabutin from about 2 mg/L to about 50.0 mg/L.

Formulations of the invention may be for any parenteral administration. For example, the composition may be formulated for injection or infusion or inhalation. The injection may be subcutaneous or intravenous. Preferably, the composition is formulated for intravenous administration. Accordingly, formulations of the invention may also include a pharmaceutically acceptable diluent. The pharmaceutically acceptable diluent may be in a concentration sufficient to deliver a therapeutically effective amount of rifabutin in IV formulation to a patient suffering from an infection. The pharmaceutically acceptable diluent may be saline. Preferably, the diluent is 0.9% saline. The solution may be administered with a therapeutically effective amount of rifabutin to treat a patient suffering from an infection.

In certain aspects, the disclosure provides a method of treating *A. baumannii* infection. The method includes administering to a patient a composition comprising rifabutin at a dose sufficient for activation of a ferric-coprogen (FhuE) receptor of *A. baumannii* cells, to thereby facilitate entry of said rifabutin into said *A. baumannii* cells. Preferably, the composition is administered intravenously. The dose may provide an AUC and $C_{max}$ associated with activation of the FhuE receptor, e.g., preferably a $C_{max}$ greater than about 2 mg/L. The $C_{max}$ may be greater than about 2 mg/L and less than about 50 mg/L. In some embodiments, $C_{max}$>2 mg/L but <50 mg/L and AUC>10 mg*h/L and <300 mg*h/L. The rifabutin may be administered In preferred embodiments, the composition includes the rifabutin, water, a solvent, and an acid. The composition is delivered intravenously at a rifabutin dose that is at least about 2 mg/kg q24 h, 1 mg/kg q12 h, or 0.5 mg/kg q6 h. The solvent may be, for example, polyoxyethylene sorbitan monooleate (Tween 80), sorbitan monooleate polyoxyethylene sorbitan monolaurate (Tween 20), polyethylene glycol (PEG), propylene glycol, N-methyl-2-pyrrolidone (NMP), glycerin, ethanol, dimethylacetamide (DMA), diethylene glycol monoethyl ether (transcutol HP), or dimethyl isosorbide (DMI). The composition may have about 2:1 v/w solvent:rifabutin. The method preferably includes delivering the formulation to the patient by intravenous injection, for example, at a dose that results in a $C_{max}$ is that is at least about 2 mg/L. The formulation may be delivered at a dose that results in: 2 mg/L<$C_{max}$<50 mg/L; and 10 mg*h/L<AUC<300 mg*h/L. The formulation may be delivered at a dose that is at least about 2 mg/kg q24 h, 1 mg/kg q12 h, or 0.5 mg/kg q6 h.

Aspects of the disclosure provide a composition for use in treating *A. baumannii* infection, the composition comprising rifabutin, water, a solvent, and an acid. The composition is an aqueous solution with a high concentration of rifabutin (e.g., 2:1 v/w solvent:rifabutin) that activates a ferric-coprogen (FhuE) receptor of *A. baumannii* cells, to thereby facilitate entry of said rifabutin into said *A. baumannii* cells. The solvent may be, for example, polyoxyethylene sorbitan monooleate (Tween 80), sorbitan monooleate polyoxyethylene sorbitan monolaurate (Tween 20), polyethylene glycol (PEG), propylene glycol, N-methyl-2-pyrrolidone (NMP), glycerin, ethanol, dimethylacetamide (DMA), diethylene glycol monoethyl ether (transcutol HP), or dimethyl isosorbide (DMI). In a preferred embodiment, the solvent is DMI or trascutol HP.

In certain embodiments, the solvent to water ratio v/v is 1:1 or 1:2. The acid may be hydrochloric, methanesulfonic, phosphoric, L-tartaric, D-glucuronic, L-malic, D-gluconic, L-lactic, acetic, or L-aspartic acid. In preferred embodiments, the acid is acetic acid or D-glucuronic acid. In certain embodiments, the rifabutin to acid molar ratio is 1:1.

Preferably, the composition is provided as an aqueous solution for intravenous delivery. The composition may be provided for a patient identified as infected with *A. baumannii*, and the composition may include rifabutin for IV delivery at a dosage that is at least about 2 mg/kg q24 h, 1 mg/kg ql2h, or 0.5 mg/kg q6 h.

In related aspects, the disclosure provides a use of rifabutin for the manufacture of a medicament for treating *A. baumannii* infection in a patient. The medicament may provide a dose that results in an AUC and $C_{max}$ associated with activation of the FhuE receptor. Preferably the medicament is prepared to be administered in a dosage regime that results in a $C_{max}$ in the patient that is that is at least about 2 mg/L. The medicament may include rifabutin, water, a solvent, and an acid. The solvent may be, for example, polyoxyethylene sorbitan monooleate (Tween 80), sorbitan monooleate polyoxyethylene sorbitan monolaurate (Tween 20), polyethylene glycol (PEG), propylene glycol, N-methyl-2-pyrrolidone (NMP), glycerin, ethanol, dimethylacetamide (DMA), diethylene glycol monoethyl ether (transcutol HP), or dimethyl isosorbide (DMI). The medicament may be provided within an IV bag. Preferably the medicament provides a dose that results in: 2 mg/L<$C_{max}$<50 mg/L; and 10 mg*h/L<AUC<300 mg*h/L. In certain embodiments, the medicament provides a rifabutin dosage that is at least about 2 mg/kg q24 h, 1 mg/kg q12 h, or 0.5 mg/kg q6 h.

In another aspect, the invention provides methods of preparing an intravenous formulation of rifabutin. The method may include preparing a solution containing a solvent and distilled water. Preferably, the solution is in a 1:1 ratio. The solvent may be any solvent but is preferably DMI. An acid may be added to the solution. The acid may be suitable to promote dissolution of rifabutin. The acid may be any acid, but preferably acetic acid. Rifabutin may be introduced into the solution containing the acid. Thus, the acid causes the rifabutin to dissolve into the solution.

The rifabutin solution may be added to a pharmaceutically acceptable diluent. The diluent may be 0.9% saline. The intravenous formulation of rifabutin may comprise rifabutin, DMI, and saline. The w/v ratio of rifabutin to solvent may be from about 4:1 to about 1:4, from about 2:1 to about 1:3, or from about 1:1 to about 1:2. The w/v ratio of rifabutin to solvent may be about 4:1, about 3:1, about 2:1, about 1:1, about 1:2, about 1:3, or about 1:4. The amount and concentration of rifabutin, DMI and saline will depend on the size of the IV bag (in intravenous embodiments) and such variations will be apparent to those of ordinary skill in the art to achieve preferred doses in the range of 6-9 mg/kg with the DMI amount determined based on the above ratios. The intravenous formulation of rifabutin may be administered to a subject in need of treatment.

In another aspect, the invention provides methods of increasing the efficacy of an antibiotic. The methods include modulating a TonB-dependent siderophore receptor in a bacteria cell to increase uptake of an antibiotic. Modulating a TonB-dependent siderophore receptor may include administering an IV formulation of an antibiotic that mediates transporting the antibiotic across a cell membrane of the bacterial cell. The TonB-dependent siderophore receptor may be an FhuE receptor. Administration of the IV formulation of the antibiotic increases bioavailability of the antibiotic, thereby increasing uptake of the antibiotic through the bacterial cell membrane. The antibiotic may be any form of rifabutin capable of being administered by IV. A siderophore may be bound to an iron complex. Rifabutin may bind to the iron-loaded siderophore or may use the mediation of the TonB-dependent siderophore receptor of the iron-loaded siderophore to cross the cell membrane. The IV formulation may be that of any IV formulation of rifabutin described herein or dose thereof.

In another aspect, the invention provides methods of treating a bacterial infection. The methods may include administering a liquid formulation of rifabutin to a subject with a bacterial infection. The liquid formulation may include rifabutin or a salt thereof, a solvent and an acid. The liquid formulation may be a solution of rifabutin and a diluent to be administered intravenously to a subject with a bacterial infection. The rifabutin may then travel across an outer membrane of a bacteria cell causing the infection and eradicate the bacteria cell. The bacterial infection may be any infection caused by *A. baumannii*, such as, but not limited to, bacteremia, Ventilator-Associated Bacterial Pneumonia (VABP), Hospital-Acquired Bacterial Pneumonia (HABP) and Urinary Tract Infections (UTI). The formulation for IV administration may include a pharmaceutically acceptable solvent. The method may include administering an IV formulation of any formulation of rifabutin described herein to a subject suffering from a bacterial infection. Without being bound to theory, any formulations of the invention may be used in any of the methods of the invention.

In another aspect, methods of the invention may include identifying compounds having *Acinetobacter baumannii* antibacterial activity. The methods may include providing a medium comprising at least an iron complex and an iron chelator, introducing a plurality of *A. baumannii* bacteria cells into the medium, and exposing the medium containing the plurality of bacteria cells to a compound. The method may also include quantifying the plurality of bacteria cells using any acceptable methods of bacteria quantification. Identifying a decrease of a number of the plurality of bacteria cells is indicative of antibacterial activity of the compound.

A decrease in the number of the plurality of bacteria cells may occur when the compound crosses an outer membrane of the bacteria cells, thereby destroying the bacteria cells. The compound may cross the outer membrane in the presence of the iron complex or the iron chelator, thus enabling Ton-B siderophore receptor mediated uptake of the compound. The receptor may be an FhuE receptor.

The medium may be Roswell Park Memorial Institute (RPMI) medium, 10% fetal calf serum, or a combination thereof. The medium may be any medium or may be any media that either contains iron and an iron chelator or is capable of having iron and an iron chelator added to the media. The iron complex may be any iron complex capable of binding to a siderophore. The iron chelator may be any iron chelator capable of crossing a bacterial cell membrane. Preferably, the iron chelator is pyridoxal isonicotinoyl hydrazone (PIH). The chelator may be present in concentrations from about 0.05 mM to 0.25 mM, from about 0.075 mM to 0.225 mM, from about 0.1 mM to 0.2 mM from about 0.125 mM to 0.15 mM. Preferably, the iron chelator is present at about 0.1 mM.

In another aspect of the invention, methods include treating a bacterial infection in a subject. The method may include administering a therapeutically effective amount of an intravenous formulation of rifabutin or a salt thereof. The formulation has a pharmaceutically acceptable solvent present at a ratio of 4:1 to about 1:4, from about 2:1 to about 1:3, or from about 1:1 to about 1:2 w/v of rifabutin to solvent.

The bacterial infection may be any infection caused by *A. baumannii*, such as, but not limited to, bacteremia, Ventilator-Associated Bacterial Pneumonia (VABP), Hospital-Acquired Bacterial Pneumonia (HABP) and Urinary Tract Infections (UTI). Preferably, the bacteria species is *A. baumannii*.

Aspects of the invention may also include an in vitro method of determining susceptibility of a species of bacteria to rifabutin. The method may include exposing a plurality bacteria cells to an iron complex, an iron chelator, and rifabutin. The method may also include quantifying a number of the plurality of bacteria cells and/or identifying a decrease in the number of bacteria cells. A decrease in the number of bacteria cells is indicative of the susceptibility of a species of bacteria to rifabutin. The method may also include administering rifabutin to a subject suffering from a bacterial infection of the species of bacteria.

Other aspects and advantages of the invention are apparent upon consideration of the following detailed description thereof.

BRIEF DESCRIPTION OF THE DRAWINGS

FIG. 1 is a graph illustrating the quantification of fhuE expression levels in *A. baumannii* HUMC1 in different media.

FIG. 2 is a graph of the activity of IV administration of rifabutin in a murine neutropenic sepsis model.

FIG. 3 shows effects of rifabutin in neutropenic lung infection mouse models with CD-1 mice infected with *A. baumannii* UNT091.

FIG. 4 shows effects of rifabutin in neutropenic lung infection mouse models with CD-1 mice infected with *A. baumannii* UNT093.

FIG. 5 provides results of dose fractionation experiments indicating a clear dose response relationship for which both $C_{max}$ and AUC are critical for activity.

FIG. 6 is a graph showing CFU per lung pair in mice inoculated with *A. baumannii*.

FIG. 7 shows a schematic of TonB-dependent transport.

FIG. 8 shows activity of rifabutin and rifampicin antibiotics upon plasmid mediated expression of FhuE-variants in CA-MHB.

DETAILED DESCRIPTION

Embodiments of the disclosure provide methods, uses, and compositions for treating, or making a medicament for treating, *A. baumannii* infection. For background, see Howard, 2012, *Acinetobacter baumannii*: An emerging opportunistic pathogen, Virulence 3(3):243-250 and Peleg, 2008, *Acinetobacter baumannii*: Emergence of a successful pathogen, Clin Microbiol Rev 21(3):538-582, both incorporated by reference. Methods and compositions of the disclosure operate through the activation of a ferric-coprogen (FhuE) receptor to facilitate entry of said rifabutin into said *A. baumannii* cells. The FhuE receptor is discussed in Sauer, 1987, Ferric-coprogen receptor FhuE of *Escherichia coli*:

Processing and sequence common to all TonB-dependent outer membrane receptor proteins, J Bact 169(5):2044-2049, incorporated by reference.

Methods preferably include obtaining a sample from a patient suspected of having an infection; performing a test on the sample to identify an infection of *A. baumannii* in the patient; and providing a formulation of rifabutin for treating the patient that, when administered to the patient, maximizes a resultant AUC and $C_{max}$. The method may include administering the formulation of rifabutin to the patient. Preferably the formulation includes rifabutin, water, a solvent, and an acid. Preferred solvents include polyoxyethylene sorbitan monooleate (Tween 80), sorbitan monooleate polyoxyethylene sorbitan monolaurate (Tween 20), polyethylene glycol (PEG), propylene glycol, N-methyl-2-pyrrolidone (NMP), glycerin, ethanol, dimethylacetamide (DMA), diethylene glycol monoethyl ether (transcutol HP), dimethyl isosorbide (DMI), or another polar solvent. The formulation may about 250 mg/ml (1:1 v/v solvent/water) or about 166.7 mg/ml (2:1 solvent/water), however concentrations of the reconstituted solution may be as high as about 300 mg/ml. In certain embodiments, the formulation is delivered to the patient, e.g., by intravenous injection. Preferably, the IV injection results in a $C_{max}$ is that greater than about 2 mg/L and optionally less than about 50 mg/L. In some embodiments, the formulation comprises a dose of rifabutin having a $C_{max}>2$ mg/L but <50 mg/L and AUC>10 mg*h/L and <300 mg*h/L. The formulation may be delivered at a dose that is at least about 2 mg/kg q24 h, 1 mg/kg q12 h, or 0.5 mg/kg q6 h. With reference to FIG. 5, the formulation is preferably delivered via IV at a dose that is at least about 2 mg/kg q24 h, 1 mg/kg q12 h, or 0.5 mg/kg q6 h.

Methods and compositions of the disclosure exploit the insight that the *A. baumannii* siderophore receptor FhuE plays an important role in rifabutin uptake.

FIG. 1 shows that fhuE is at least 10-fold overexpressed when *A. baumannii* is grown in nutrient depleted medium (Roswell Park Memorial Institute (RPMI) medium plus 10% fetal calf serum (FCS)) compared to standard testing conditions (cation-adjusted Mueller Hinton broth; CA-MHB). As shown in the Examples, deletion of fhuE resulted in elevated MICs towards rifabutin in RPMI+10% FCS however, surprisingly had no effect on the closely related compound rifampicin. These results confirmed that FhuE is required for potent rifabutin activity in RPMI+10% FCS and indicated that rifabutin activity in this medium is likely due to active uptake of the compound mediated by the *A. baumannii* siderophore receptor FhuE.

Figure 5:
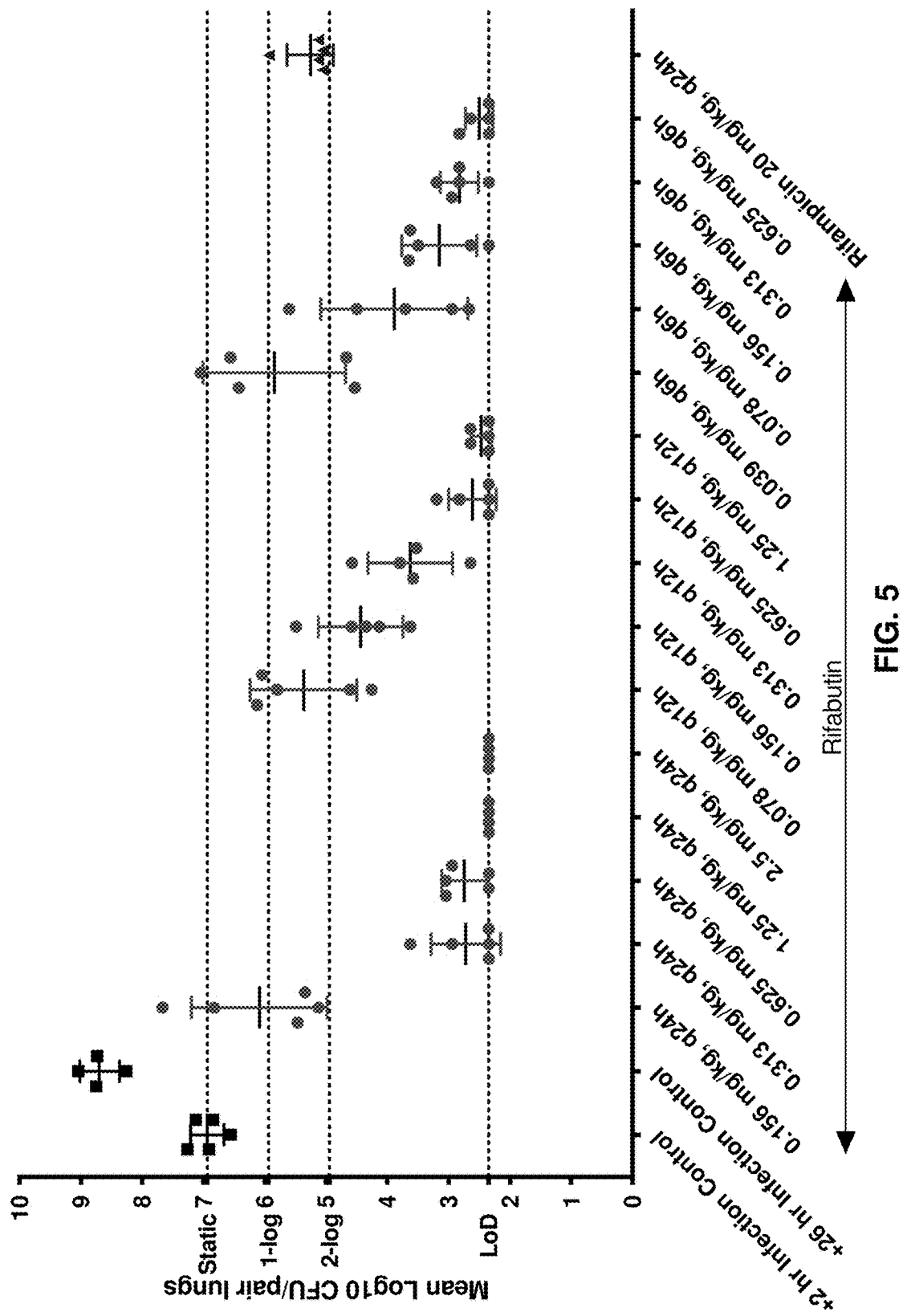

FIG. 5 provides results of dose fractionation experiments indicating a clear dose response relationship for which both $C_{max}$ and AUC are critical for activity.

In preferred embodiments, the disclosure provides methods of treating *A. baumannii* infection by administering rifabutin in an amount that maximize the AUC and $C_{max}$. The administration may be achieved by intravenous injection or by methods known in the art for modified oral released or by inhalation if locally high $C_{max}$ and AUC are required.

In certain embodiments, rifabutin is administered as an intravenous formulation in an amount that maximize the AUC and $C_{max}$. By such methods, rifabutin will reach therapeutic concentrations and reduce the frequency of resistance development. For example, in preferred embodiments, $C_{max}$ is greater than about 2 mg/L and less than about 50 mg/L.

Embodiments of the disclosure provide a composition that includes rifabutin. In certain aspects, the disclosure provides a composition for use in treating *A. baumannii* infection, the composition comprising rifabutin, water, a solvent, and an acid. The solvent may be polyoxyethylene sorbitan monooleate (Tween 80), sorbitan monooleate polyoxyethylene sorbitan monolaurate (Tween 20), polyethylene glycol (PEG), propylene glycol, N-methyl-2-pyrrolidone (NMP), glycerin, ethanol, dimethylacetamide (DMA), diethylene glycol monoethyl ether (transcutol HP), or dimethyl isosorbide (DMI). The composition may include between about 1:1 and 2:1 v/v solvent/water. Most preferably, the composition is provided within an IV bag. In preferred embodiments, the composition is provided for a patient identified as infected with the *A. baumannii*, and the composition includes rifabutin for IV delivery at a dosage that is at least about 2 mg/kg q24 h, 1 mg/kg q12 h, or 0.5 mg/kg q6 h. The composition may have a formulation that provides for a dose of rifabutin having a $C_{max}>2$ mg/L but <50 mg/L and AUC>10 mg*h/L and <300 mg*h/L.

Preferably, the formulation is intended for intravenous delivery.

In other aspects, the disclosure provides a use of rifabutin for the manufacture of a medicament for treating *A. baumannii* infection in a patient, in which the medicament is prepared to be administered in a dosage regime that results in a $C_{max}$ in the patient that is that is at least about 2 mg/L. Preferably, the medicament comprises rifabutin, water, an acid, and a solvent (e.g., polyoxyethylene sorbitan monooleate (Tween 80), sorbitan monooleate polyoxyethylene sorbitan monolaurate (Tween 20), polyethylene glycol (PEG), propylene glycol, N-methyl-2-pyrrolidone (NMP), glycerin, ethanol, dimethylacetamide (DMA), diethylene glycol monoethyl ether (transcutol HP), or dimethyl isosorbide). In a preferred embodiment, the solvent is DMI or trascutol HP. In certain embodiments, the solvent to water ratio v/v is 1:1 or 1:2. The acid may be hydrochloric, methanesulfonic, phosphoric, L-tartaric, D-glucuronic, L-malic, D-gluconic, L-lactic, acetic, or L-aspartic acid. In a preferred embodiment, the acid is acetic acid or D-glucuronic acid. In certain embodiments, the rifabutin to acid molar ratio is 1:1.

Most preferably, the medicament is provided within an IV bag. In preferred embodiments of the use, the dosage regime results in: 2 mg/L<$C_{max}$<50 mg/L; and 10 mg*h/L<AUC<300 mg*h/L. The dosage regime may preferably result in a dose that is at least about 2 mg/kg q24 h, 1 mg/kg q12h, or 0.5 mg/kg q6 h.

Optionally, the rifabutin may be administered by inhalation in an amount that maximize the local AUC and $C_{max}$. Such methods and compositions allow the rifabutin to reach therapeutic concentrations and reduce the frequency of resistance development.

In some embodiments, rifabutin is administered by a modified release oral drug delivery system to enhance $C_{max}$ and AUC and minimize $t_{max}$ so to maximize the AUC and $C_{max}$. Such systems and methods allow rifabutin to reach therapeutic concentrations and reduce the frequency of resistance development.

EXAMPLES

Example 1

A number of approved drugs were tested against *A. baumannii* under standard testing conditions (cation-adjusted Mueller Hinton broth; CA-MHB) as well as nutrient depleted medium (Roswell Park Memorial Institute (RPMI) medium plus 10% fetal calf serum (FCS). The antibacterial activity of rifabutin against *A. baumannii* was greatly enhanced under non-standard testing conditions. Table 1 summarizes the results of the antimicrobial susceptibilities of carbapenem resistant *A. baumannii* strains HUMC1 and UNT091 under standard (CA-MHB, Mueller Hinton broth 2) and non-standard testing conditions. The results indicate that the two carbapenem resistant *A. baumannii* strains, HUMC1 and UNT091, were highly susceptible towards rifabutin (MIC=0.002 mg/L) when tested in RPMI supplemented with 10% FCS, but showed low susceptibility for rifampin, meropenem, cefotaxime, gentamicin and ciprofloxacin. In striking contrast, both strains had low susceptibility towards all of the tested antibiotics (including rifabutin), when tested under standard testing conditions (CA-MHB broth).

colonies of bacterial strains from over-night growth on ChromAgar orientation plates (CHROMagar Cat. No. RT412) were suspended in 5 mL saline. The turbidity of the bacterial suspension was adjusted to 0.5 McFarland units (equal to an optical density at 610 nm (OD610) to 0.08-0.1). This suspension was diluted 200-fold in RPMI supplemented with 10% (v/v) FCS to reach a final concentration of approximately 106 colony forming units (CFU)/mL and was used to inoculate the microtiter plates.

Serial 2-fold dilutions of the antibiotics were prepared in a separate 96-well plate polypropylene U-bottom plate (Ratiolab Cat. No. 6018111) in RPMI supplemented with 10% (v/v) FCS at 10-fold of the final test concentrations and 10 μl of the dilutions were transferred to new 96-well polystyrene U-bottom microtiter plates with a parafilm plate cover.

The plates were then inoculated with 90 μL per well of the prepared bacterial suspensions in using a multichannel pipette (Eppendorf), with the first column containing 4 wells each for growth control (no antibiotic). The plates were covered with parafilm and incubated at 35° C. for 20-24 h, after which the MIC was determined by visual inspection and the plates were scanned to record the data. The MIC was recorded as the lowest concentration of the compound that inhibited bacterial growth by visual inspection. MICs were determined at least in duplicates and in the case of variations, the higher values are provided.

TABLE 1

Antibacterial activity of rifabutin, rifampin and comparators against *A. baumannii* in nutrient depleted and standard testing conditions

| | MIC (mg/L) | | | | | | | | | | | |
|---|---|---|---|---|---|---|---|---|---|---|---|---|
| | RPMI plus 10% FCS | | | | | | CA-MHB | | | | | |
| | rifa-butin | rifam-pin | mero-penem | cefo-taxime | genta-micin | cipro-floxacin | rifa-butin | rifam-pin | mero-penem | cefo-taxime | genta-micin | cipro-floxacin |
| HUMC1 | 0.002 | 16 | >16 | >64 | >16 | >4 | 4 | 16 | >16 | >64 | >16 | >4 |
| UNT091 | 0.002 | 16 | >16 | >64 | >16 | >4 | 8 | 8 | >16 | >64 | >16 | >4 |

Methods for Testing in Example 1, Table 1.

The in vitro activity of rifabutin, rifampin, meropenem, cefotaxime, gentamicin and ciprofloxacin against two carbapenem-resistant clinical *A. baumannii* isolates in Roswell Park Memorial Institute (RPMI) medium supplemented with 10% (v/v) fetal calf serum (FCS) and under standard minimum inhibitory concentration (MIC) assay conditions was analyzed.

Stock solutions of rifabutin were prepared at 2 mg/mL in DMSO and stored at −20° C.

Two *A. baumannii* isolates were used in this example: HUMC1 (BV374) (Spellberg/Luna Laboratory, University of Southern California, Los Angeles, Calif.) and UNT091-1 (BV378) (UNT Health Science Center, Fort Worth, Tex.). The HUMC1 isolate is a hyper-virulent drug-resistant clinical strain isolated from a blood-stream infection. Both strains are carbapenem resistant and colistin sensitive. The isolates were stored at −80° C. as 20% (v/v) glycerol cultures.

MICs were determined by the broth microdilution method following the guidelines of the Clinical Laboratory Standards Institute (CLSI) using RPMI supplemented with 10% (v/v) or cationic-adjusted Muller Hinton broth (CA-MHB) as assay medium. To prepare the bacterial inocula, 3-5

Figure 1:
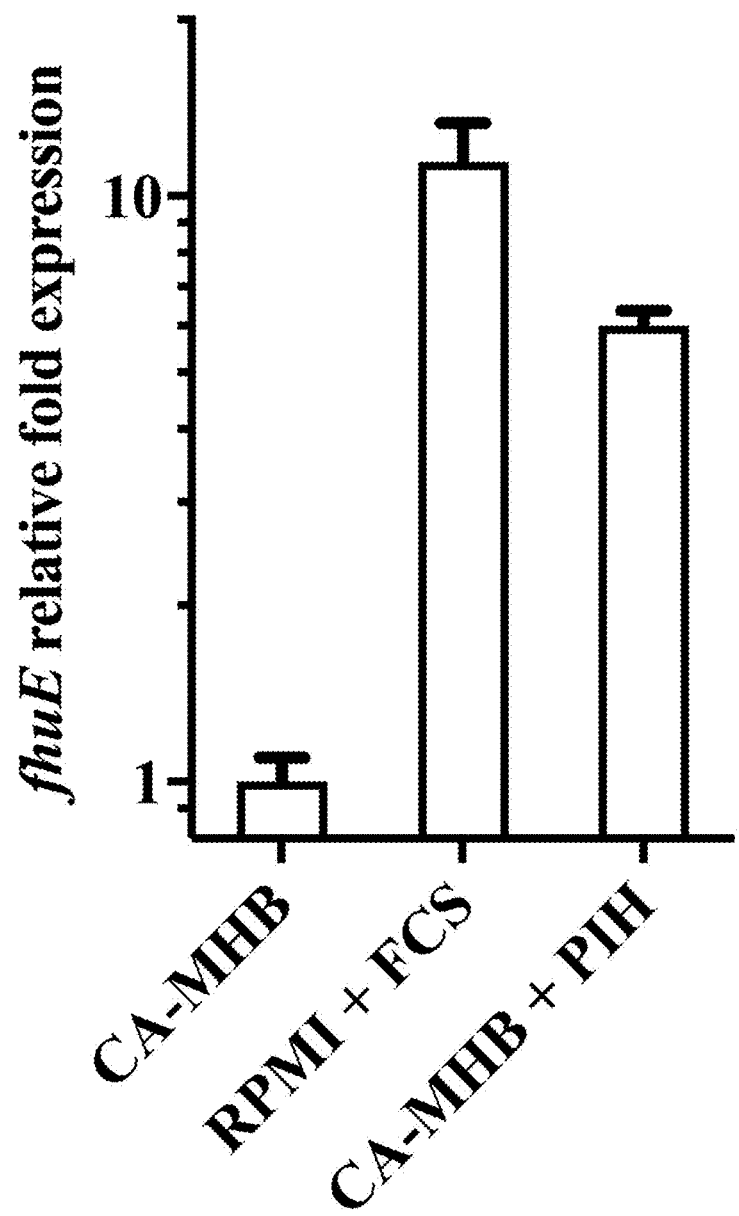

Example 2. FhuE Overexpression: The Level of fhuE Expression was Evaluated in Different Media by qRT-PCR on the *A. baumannii* HUMC1 Strain FIG. 1 depicts a graph illustrating the quantification of fhuE expression levels in different media. As depicted, fhuE is at approximately 10-fold overexpressed when *A. baumannii* is grown in RPMI+10% FCS or CA-MHB supplemented with 0.1 mM pyridoxal isonicotinoyl hydrazone (PIH) compared to CA-MHB. These results indicate that the increased rifabutin activity is due to the increased fhuE expression in these media.

Methods for Measuring fhuE Expression Levels, FIG. 1.

The expression of fhuE was evaluated by quantitative reverse transcription-PCR (qRT-PCR). Isolates were grown in specified broth at 37° C. to mid-log phase (optical density at 600 nm [OD600] of 0.5), and total RNA was extracted using a PureLink RNA minikit (Ambion) according to the manufacturer's recommendations. Residual DNA contaminations were removed using a Turbo DNA-free kit (Ambion). qRT-PCR was performed using a GoTaq 1-Step RT-qPCR System kit (Promega) on a CFX96 Touch™ Real-Time PCR Detection System (BioRad). As a housekeeping gene, the RNA polymerase sigma factor D (rpoD)

was quantified and fhuE expression was normalized to that of rpoD using the comparative MET (where CT is threshold cycle) method.

Example 3. Deletion of fhuE

To confirm the role of FhuE activation in rifabutin activity, fhuE was deleted in the *A. baumannii* strains HUMC1 and UNT091.

Table 2 summarizes MICs of rifabutin in RPMI medium supplemented with 10% (v/v) FCS for the fhuE deleted mutants and their parental strains. Deletion of fhuE resulted in elevated MICs towards rifabutin in RPMI+10% FCS however, surprisingly had no effect on the closely related compound rifampicin. These results confirmed that FhuE is required for potent rifabutin activity in RPMI+10% FCS and indicated that rifabutin activity in this medium is likely due to active uptake of the compound mediated by the *A. baumannii* siderophore receptor FhuE. The data from this experiment show that rifabutin is very active against *A. baumannii* because of a novel mechanism of entry in *A. baumannii*.

TABLE 2

Antibacterial activity of rifabutin and rifampicin FhuE depleted mutants of *A. baumannii*.

| Drug/Isolate | HUMC1 | HUMC1 ΔfhuE | UNT091 | ΔfhuE |
|---|---|---|---|---|
| rifabutin (MIC = mg/L) | 0.002 | 2 | 0.002 | 0.5 |
| rifampin (MIC = mg/L) | 32 | 32 | 2 | 4 |

Methods for Constructing the fhuE Deletion Mutant, Table 2.

The gene AWC45_RS10145 (HUMC1 genome) coding for the FhuE protein was deleted in the *A. baumannii* strains HUMC1 and UNT091 using a two-step recombination method. DNA fragments corresponding to 700-bp up and downstream genomic regions of fhuE were amplified by PCR and introduced into the pVT77 knockout plasmid using Gibson assembly. The resulting fhuE knockout plasmid was transferred in *A. baumannii* isolates by conjugation and transconjugants were selected on LB agar plates containing sodium tellurite. After overnight selection at 37° C., clones were screened for genomic plasmid integration by PCR and clones containing up- and downstream plasmid integrations were used for counter-selection on LB agar plates containing AZT for plasmid removal from the genome. Clones were screened for fhuE deletion and plasmid removal by PCR, and the genomic gene deletions were confirmed by DNA sequencing (Microsynth AG, Balgach, Switzerland).

Example 4. Plasmid-Based Expression of fhuE

Overexpression of fhuE was evaluated to determine whether it triggers rifabutin uptake.

Table 3 summarizes MICs of rifabutin in fhuE expressing *A. baumannii* strains in CA-MHB+/−1 mM IPTG. In the presence of IPTG, rifabutin MIC was 1000-fold lower in the strain carrying the fhuE expressing plasmid compared to the strain carrying an empty plasmid as control. This data shows that activation of fhuE in *A. baumannii* results in a potent activity of rifabutin towards this organism.

TABLE 3

MICs of rifabutin in fhuE expressing *A. baumannii* strains in CA-MHB +/− 1 mM IPTG

| | | rifabutin MIC (mg/L) | |
|---|---|---|---|
| Strain | Plasmid | CA-MHB no IPTG | CA-MHB 1 mM IPTG |
| *A. baumannii* ATCC 17978 | no plasmid | 4 | 4 |
| | empty plasmid | 1 | 2 |
| | FhuE expressing plasmid | 0.016 | 0.002 |

Methods for Overexpression of fhuE in *A. baumannii*, Table 3.

The fhuE gene (AWC45_RS10145) from the *A. baumannii* HUMC1 strain was cloned into the *E. coli/A. baumannii* shuttle plasmid pVT111 under the control of the isopropyl-beta-D-1-thiogalactopyranoside (IPTG) inducible promoter Ptrc-lacO. The resulting plasmid and the original pVT111 plasmid (control) were transferred to the *A. baumannii* strain ATCC-17978 by conjugation and transconjugants were selected on LB agar plates containing kanamycin. The presence of the plasmids in the receiver *A. baumannii* strains was then confirmed by PCR.

Example 5: Frequency of Mutational Resistance (FoR) Towards Rifabutin

Table 4 summaries the FoR results of the *A. baumannii* spontaneous resistance frequencies to rifabutin on RPMI+ 10% FCS agar medium. Dose-dependent FoR ranging from $10^{-5}$ to $10^{-9}$ was observed for the HUMC1 strain. High FoR's around $10^{-5}$ were observed at rifabutin concentrations of 0.02 and 0.2 mg/L, followed by a step wise decrease to $10^{-7}$ at 1 mg/L and $10^{-9}$ at 2 mg/L and 20 mg/L rifabutin. Similar results were obtained for strains UNT091-1, ACC00445, LAC-4 and UNT238-1.

TABLE 4

Frequency of Mutational Resistance (FoR) results of the *A. baumannii* spontaneous resistance frequencies to rifabutin on RPMI + 10% FCS agar medium

| rifabutin | *A. baumannii* clinical isolate | | | | |
|---|---|---|---|---|---|
| (mg/L) | HUMC-1 | UNT091 | ACC00445 | LAC-4 | UNT238 |
| 0.02 | 2.20E−05 | 7.80E−06 | 1.10E−05 | | |
| 0.1 | 1.70E−05 | | | | |
| 0.2 | 1.70E−05 | 6.40E−06 | 8.10E−06 | 7.00E−05 | 2.30E−05 |
| 1 | 4.30E−07 | | | | |
| 2 | 3.30E−09 | 7.10E−09 | 2.40E−09 | 5.00E−09 | 8.80E−10 |
| 20 | 2.10E−09 | 7.80E−09 | 5.70E−09 | 4.20E−09 | 1.60E−08 |

The five clinical *A. baumannii* strains reveal a dose dependent frequency of mutational resistance reaching $10^{-9}$ at rifabutin concentrations of ≥2 mg/L. Similar in vitro FoR ($10^{-9}$) have been demonstrated for other antibiotics used as standard of care to treat *A. baumannii* infections. The results demonstrate that rifabutin can be used to efficiently treat *A. baumannii* infections. Importantly, it was identified that the route of administration must achieve systemic drug concentrations of >2 mg/L to prevent rapid resistance development, a concentration not achievable with the currently available oral formulations.

Methods for Determining the Frequency of Mutational Resistance Towards Rifabutin, Table 4.

The frequency of *A. baumannii* mutational resistance (FoR) to rifabutin in the RPMI medium supplemented with 10% (v/v) fetal calf serum (FCS) was investigated.

Stock solutions of rifabutin were prepared at 10 mg/mL in DMSO and stored at −20° C. *A. baumannii* clinical isolates were stored at −80° C. as 20% (v/v) in glycerol stock cultures.

Selective agar plates were prepared using RPMI powder (Sigma R7755) dissolved at 10.3 g/L with agar at 15 g/L and boiled until complete agar melting. After cooling the media to 45° C., 0.3 g/L L-glutamine (Sigma G7513), 25 mM HEPES (Gibco 15630-056) and 10% (v/v) FCS (Gibco 10500-064) were added. Concentrations of 0.02, 0.1, 1.0, 2.0 and 20.0 mg/L of rifabutin were supplemented and 25 mL of the media was poured directly into 9 cm petri dishes.

The culture inocula were prepared from a bacterial NaCl suspension at 0.5 McFarland diluted 200-times in 100 mL of RPMI (Sigma R8758)+10% FCS in 500 mL flasks to reach ~$5 \times 10^5$ CFU/mL. The flasks were incubated for 24 h at 37° C. under shaking at 220 rpm. After incubation, the cells were pelleted by centrifugation (10 min, 7000 rpm at RT) and re-suspended in 1 mL PBS. Ten-fold dilution series of the cell suspensions were prepared in PBS and 100 of the resulting cell suspension were inoculated on the rifabutin containing selection plates described above, as well as on non-selective plates to determine the cell density of the inocula. After incubation at 35° C. for 24 h colonies were counted, and the frequency of resistance was calculated as the ratio between the number of colonies growing on plates with antibiotic and the total colony count of the inocula.

Example 6: In Vivo Studies

Figure 2:
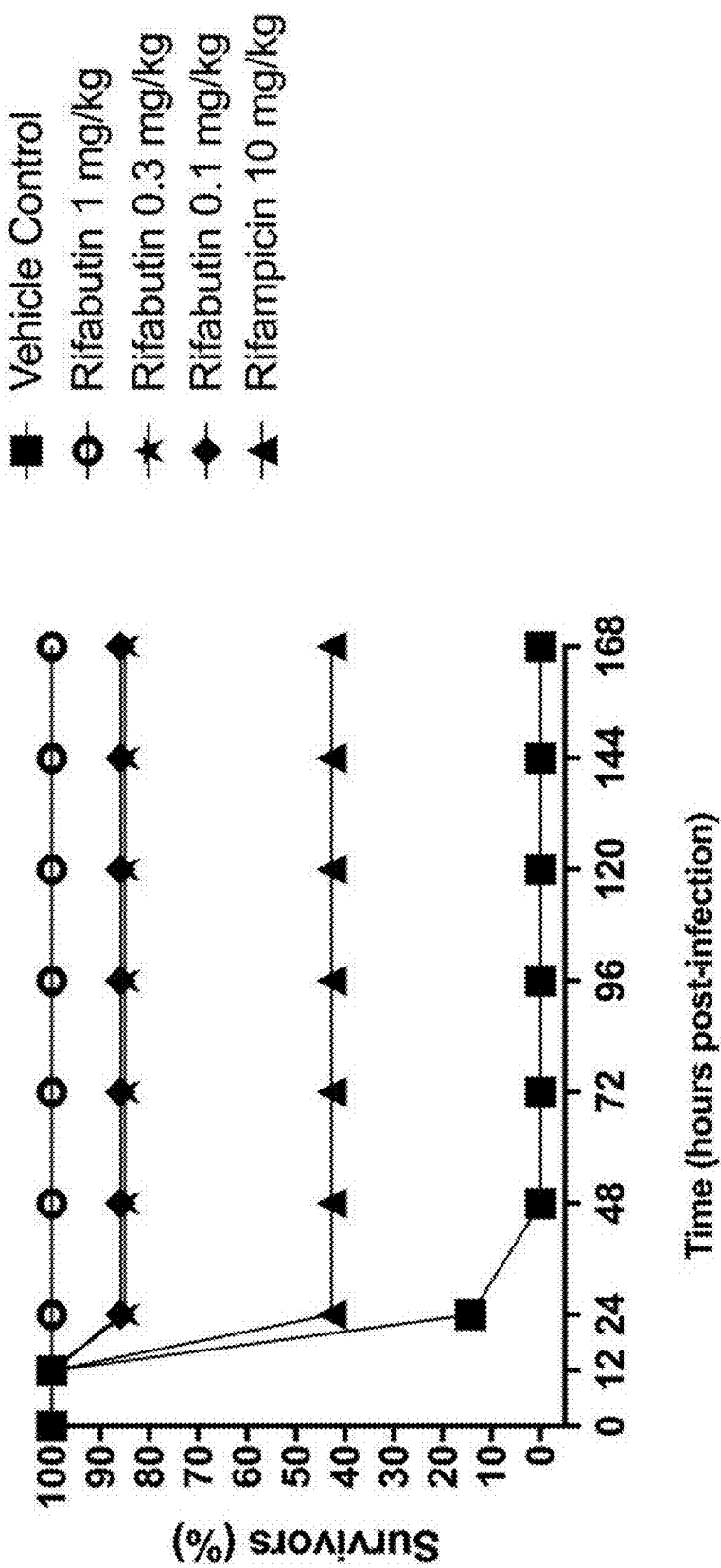
FIG. 2 is a graph illustrating the results of the effect of rifabutin and rifampin in a neutropenic sepsis mouse model. The results indicate that the IV administration of rifabutin protects against sepsis with a dose dependent response at 1 mg/kg whereas rifampin does not at 10 mg/kg supporting the potent activity of rifabutin observed in vitro.

FIG. 2 is a graph illustrating the results of the effect of rifabutin and rifampin in a neutropenic sepsis mouse model (n=7). The CD-1 mice were IP infected with *A. baumannii* ACC00445 strain in the presence of 5 mucin. The mice were treated with rifabutin and rifampin via IV administration at 1 h and 5 h post-infection. The results indicate that the IV administration of rifabutin protects against sepsis with a dose dependent response at 1 mg/kg whereas rifampin does not at 10 mg/kg supporting the potent activity of rifabutin observed in vitro.

Figure 3:
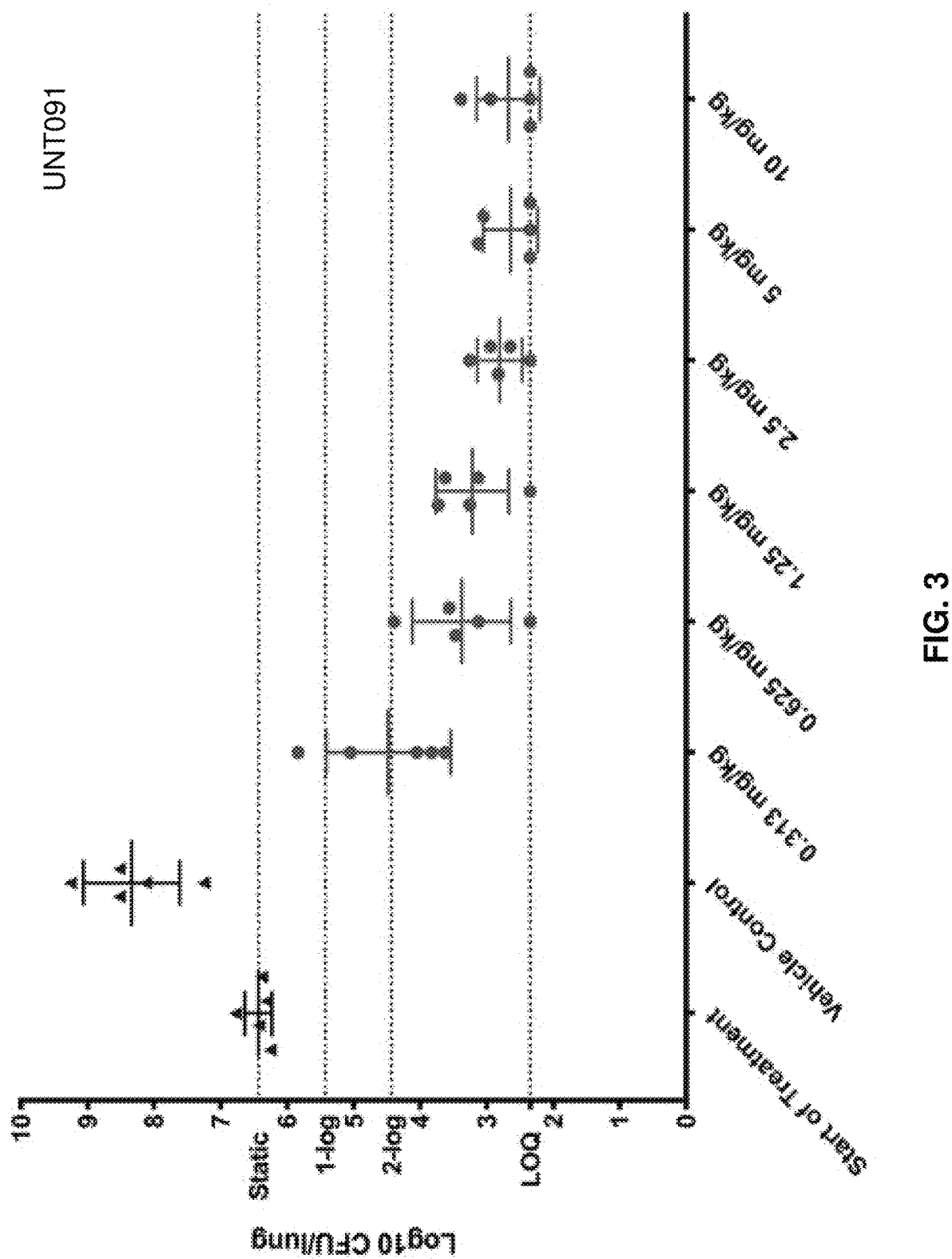
FIG. 3 shows effects of rifabutin in neutropenic lung infection mouse models with CD-1 mice infected with *A. baumannii* UNT091.

FIG. 3 is a graph illustrating the results of the effect of rifabutin in neutropenic lung infection mouse models (n=5/ dose group) in which the CD-1 mice were intranasally infected with *A. baumannii* UNT091. The mice were treated with rifabutin via IV administration at 2 h post-infection.

Figure 4:
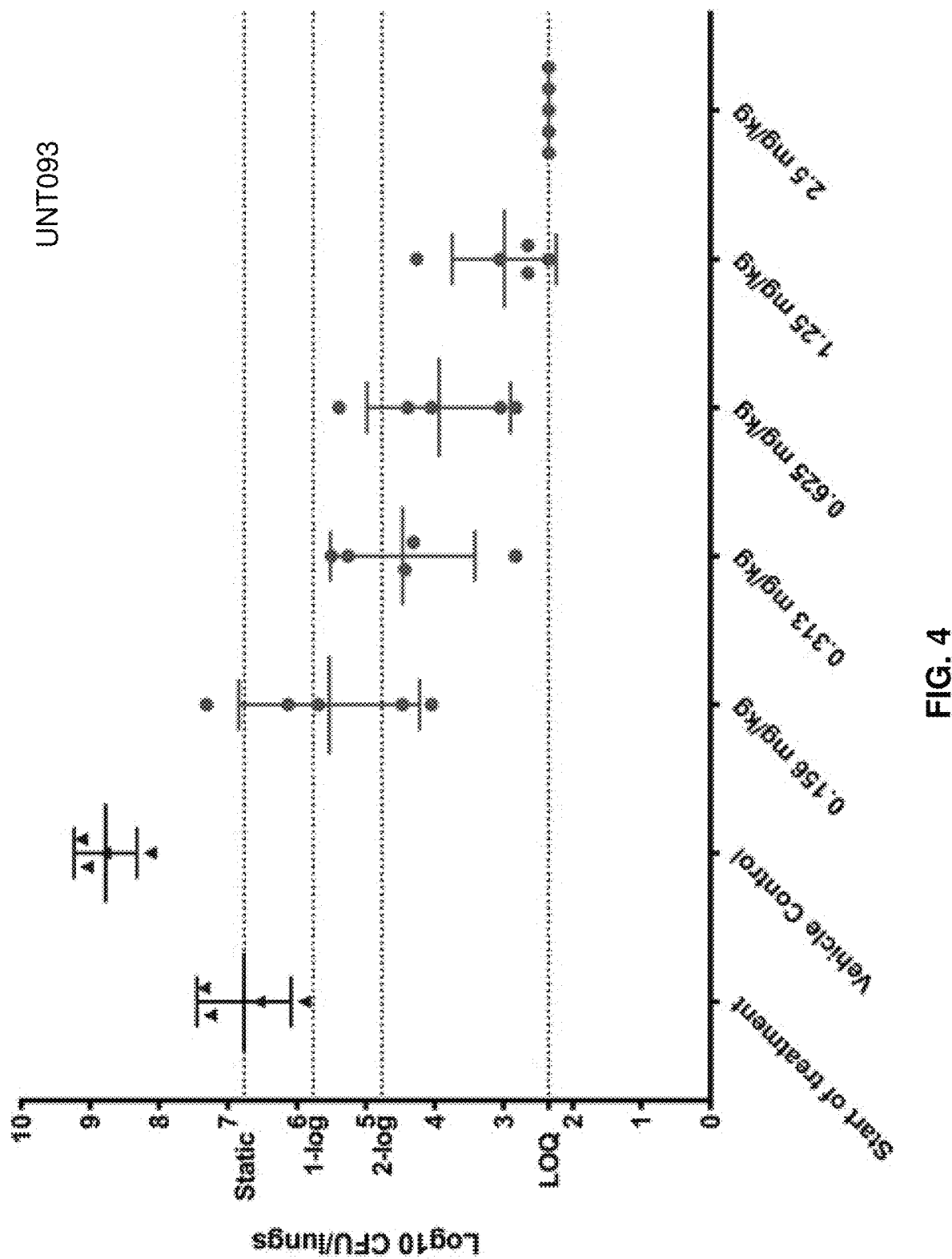
FIG. 4 shows effects of rifabutin in neutropenic lung infection mouse models with CD-1 mice infected with *A. baumannii* UNT093.

FIG. 4 is a graph illustrating the results of the effect of rifabutin in neutropenic lung infection mouse models (n=5/ dose group) in which the CD-1 mice were intranasally infected with *A. baumannii* UNT093. The mice were treated with rifabutin via IV administration at 2 h post-infection.

After 24 hours of treatment the mice were sacrificed and colony forming units in the lungs were measured. The results indicate the IV administration of rifabutin results in a potent effect at doses of <0.5 mg/kg supporting the potent activity of rifabutin observed in vitro.

FIG. 5 summarizes the results of dose fractionation experiments in a neutropenic mouse model of infection. Rifabutin was administered IV either once daily (q24 h), bi-daily (q12 h) or four-times within 24 hours (q6 h). The results indicate a clear dose response relationship for which both $C_{max}$ and AUC are critical for activity.

Table 5 is the target exposures required to treat *A. baumannii* infections based upon MIC. The estimations are based on efficacy models and using a sigmoid Emax model with variable slope to fit the dose and PK/PD index (PDI) responses to determine the PDI values of rifabutin resulting in 1-log reduction in lung CFUs using GraphPad Prism version 5.03 (GraphPad, Inc., San Diego, Calif.). From this data it is evident that the oral administration of rifabutin will not achieve the exposures required to treat >90% of the *A. baumannii* isolates (MIC<1 mg/L).

TABLE 5

Target exposures required to treat *A. baumannii* infections based upon MIC

| MIC (mg/L) | $C_{max}$ (mg/L) | AUC (mg*h/L) |
|---|---|---|
| 0.125 | 0.32 | 1.44 |
| 0.25 | 0.65 | 2.87 |
| 0.5 | 1.30 | 5.74 |
| 1 | 2.59 | 11.48 |
| 2 | 5.19 | 22.96 |

The in vivo studies demonstrate the IV administration of rifabutin is as potent and effective in vivo as in vitro. Thus, the unexpected finding that rifabutin displays a potent activity towards *A. baumannii* under nutrient limiting conditions (specifically iron limiting conditions) due to the activation and uptake into the bacterial cell via the fhuE siderophore transporter allows for a potent activity in mouse models of infection. Particularly, IV formulation of rifabutin are effective against *A. baumannii* infections.

Figure 6:
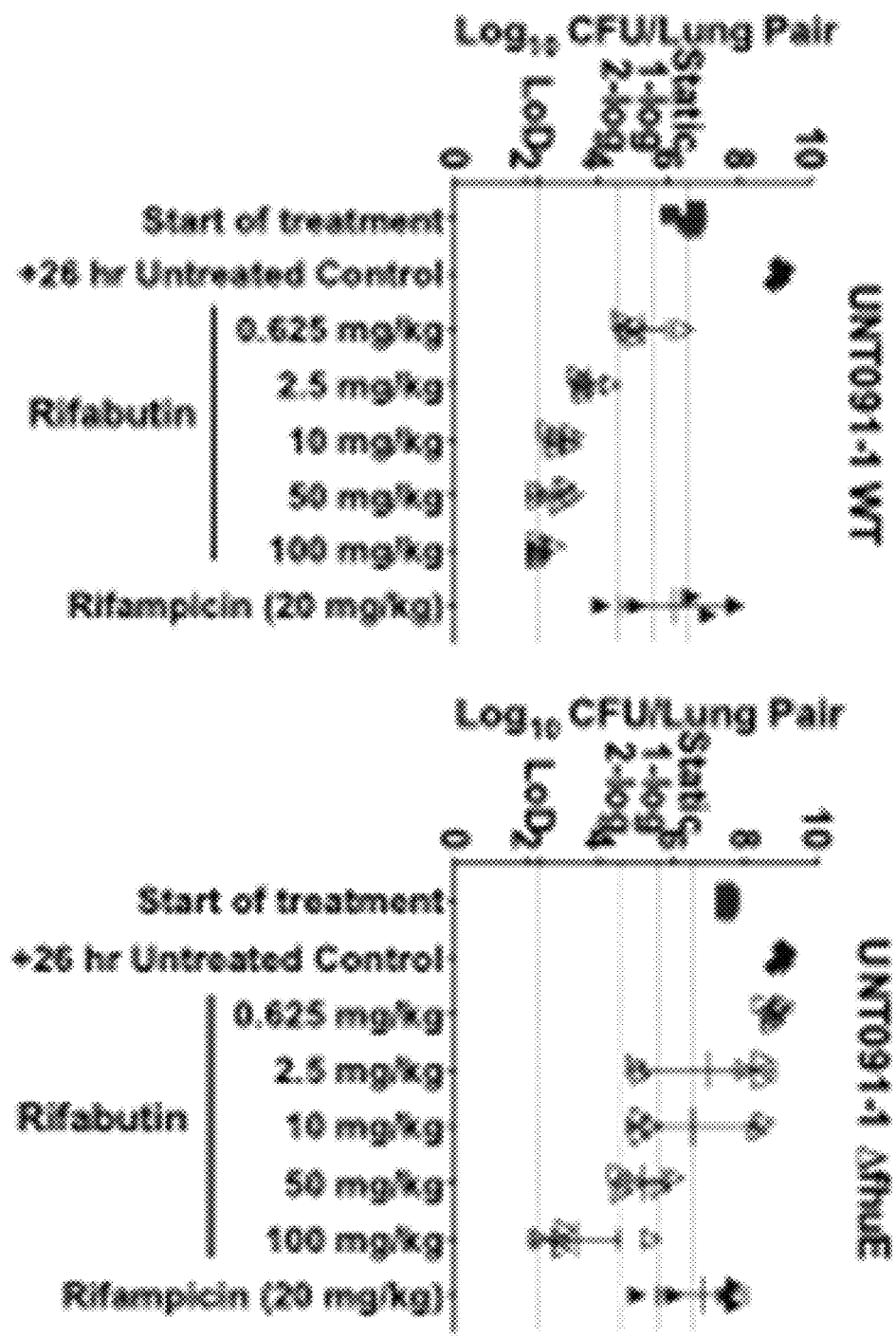

FIG. 6 is a graph showing CFU per lung pair in mice inoculated with *A. baumannii* strains. Neutropenic, female CD-1 mice (5 per group) were inoculated intranasally (t=0 hr) with equivalent titers (6.90 and 6.93 $\log_{10}$ CFU) of *A. baumannii* UNT091-1 wildtype and *A. baumannii* UNT091-1 ΔfhuE mutant. The treatment (single IV dose) was administered at 2-hour post-infection and bacterial burden was reported at 26 hours by determining CFU/lung. Furthermore, the effect of RBT was blunted in mice infected with the UNT091-1::ΔfhuE strain supporting the role of fhuE as mediating RBT sensitivity both in vitro and in vivo.

Example 7: The In Vitro Activity of Rifabutin was Determined Towards a Panel of Clinical *A. baumannii* in the Presence of an Iron Chelator Leading to Increased Siderophore Receptor Expression Rifabutin displays a potent in vitro activity against a large panel of recently isolated and mainly XDR *A. baumannii* including isolates non-susceptible to colistin, and carbapenems. Complexation of free iron by PIH allows robust rifabutin susceptibility testing in nutrient rich standard MHA.

All isolates were resistant to carbapenems. Rifabutin showed excellent activity towards *A. baumannii* with an MIC50/MIC90 of 0.008/1 mg/L in iron-chelated nutrient rich MHA, comparable to liquid MIC determination using RPMI supplemented with FCS (MIC50/MIC90 of 0.004/2 mg/L). In contrast, in standard MHA rifabutin had only marginal activity.

Methods for Determining In Vitro Activity

A panel of 293 CRAB strains isolated from Europe (n=144), United States of America (USA) (n=99) and Asia-West Pacific (n=50) regions between 2017-2019 was used for rifabutin MIC determination. The strain panel contained isolates with 10% MDR (n=29), 86% XDR (n=253) and 4% (n=11) PDR phenotypes. Isolates were collected mainly from patients with pneumonia (59%), bloodstream infections (28%), and skin and soft tissue infections (11%) and categorized according to CLSI breakpoints as XDR when non-susceptible to <2 of the antimicrobial classes described by Magiorakos et al. 2011. Susceptibility testing of *A. baumannii* with rifabutin was performed using agar dilution method with Muller Hinton Agar (MHA) supplemented with 0.1 mM pyridoxal isonicotinoyl hydrazine (PIH), a potent nontoxic iron chelator. Comparator antibiotics were tested at CLSI standard conditions.

Example 8: Modeling FhuE TonB Effects on Rifabutin Activity

Figure 8:
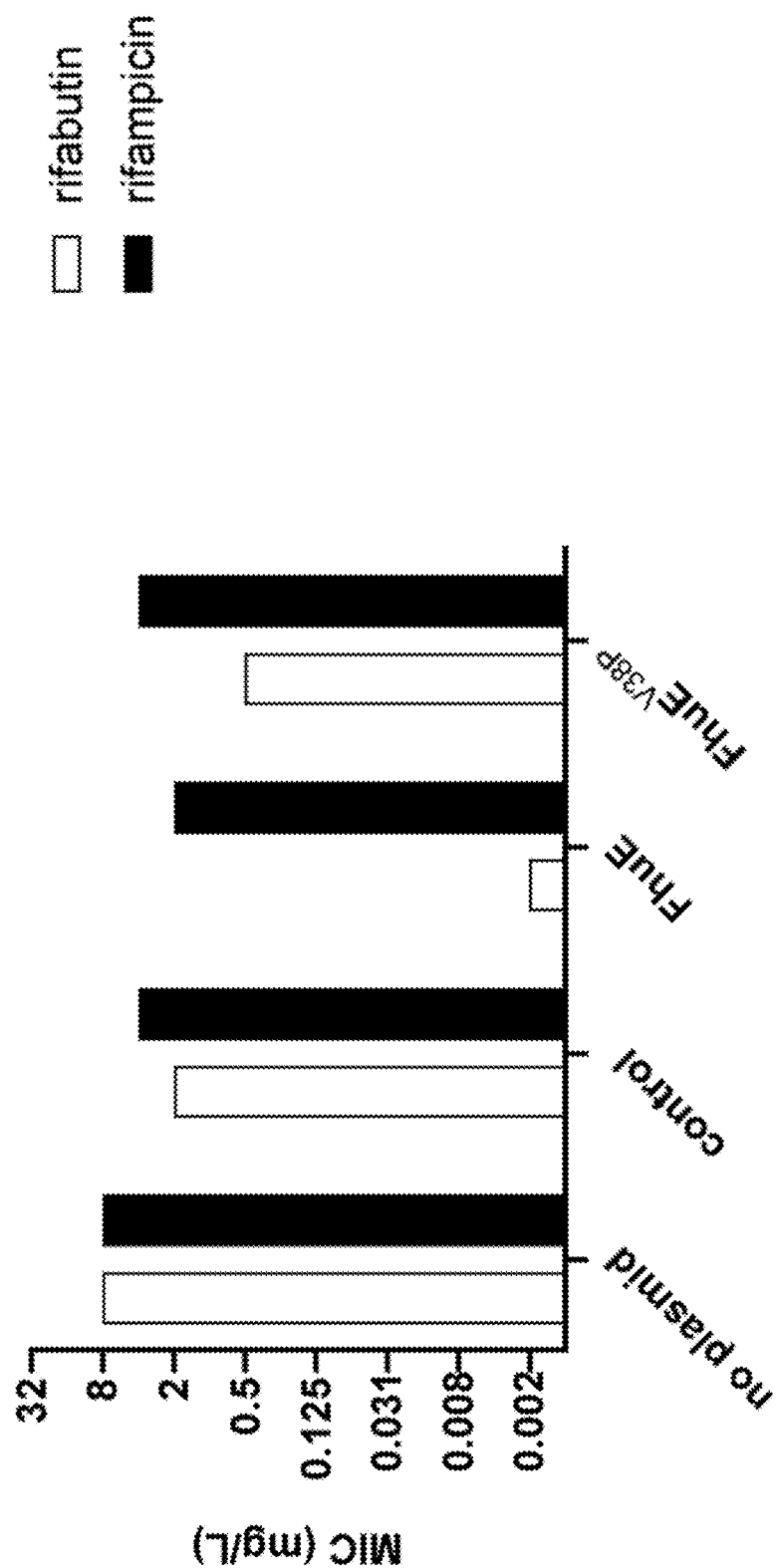

In complementation assays, FhuE V38P expression was not able to restore rifabutin potent activity compared to wildtype FhuE expression indicating that physical interaction between the FhuE TonB box and the TonB energy transducing machinery is required for rifabutin potent activity as shown in FIG. 8. These data suggest that rifabutin binding to FhuE is required to activate FhuE allosteric conformational transition enabling rifabutin active transport and potent activity against *A. baumannii*. FIG. 8 shows activity of rifabutin and rifampicin antibiotics upon plasmid mediated expression of FhuE-variants in CA-MHB. *A. baumannii* ATCC-17978 was used as host strain, gene expression from plasmids was induced with 1 mM IPTG and a plasmid that did not encode fhuE was used as control.

Methods for Measuring TonB Effects on Rifabutin Activity

Figure 7:
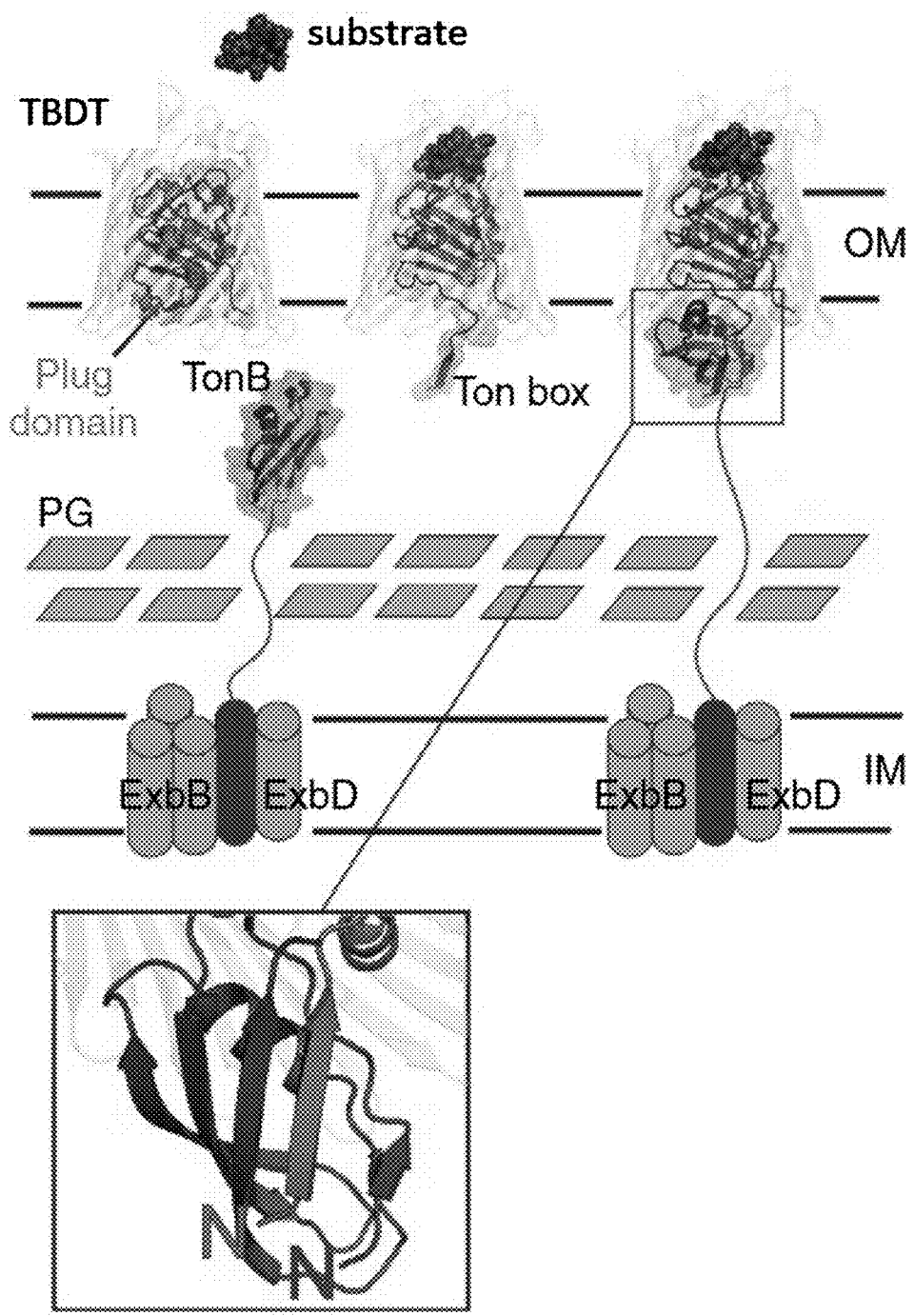

Potent rifabutin activity against *A. baumannii* is dependent on the expression of the TonB-dependent transporter (TBDT) FhuE suggesting that rifabutin is actively translocated across *A. baumannii* outer membrane through FhuE. TBDT mediated active transport requires specific substrate binding to activate allosteric conformational transition of the transporter leading to the recruitment of the TonB energy transducing machinery through the so-called TonB box of the TBDT as shown in FIG. 7. See, Noinaj, N., Guillier, M., Barnard, T. J. & Buchanan, S. K. TonB-dependent transporters: regulation, structure, and function. Annu. Rev. Microbiol. 64, 43-60 (2010), incorporated herein by reference. FIG. 7 shows a schematic of TonB-dependent transport adapted from Hickman, S. J., Cooper, R. E. M., Bellucci, L., Paci, E. & Brockwell, D. J. Gating of TonB-dependent transporters by substrate-specific forced remodelling. Nat. Commun. 8, 1-12 (2017), incorporated herein by refrence. TBDTs are so-called gated porins with their lumen occluded by an N-terminal plug domain preventing the substrate to transit across the outer membrane. The binding of substrate induces an allosteric rearrangement of the plug domain, releasing the Ton box into the periplasmic space, where it recruits the C-terminal domain of TonB in complex with ExbB and ExbD to form the energy transducing machinery. Linkage of the OM and IM via this non-covalent complex is required to trigger the full or partial unfolding of the plug domain, allowing the passage of the substrate. TBDT: TonB-dependent transporter, OM: outer membrane, IM: inner membrane, PG:

peptidoglycan.

To investigate if rifabutin is actively transported, a FhuE V38P mutant was generated that carries a mutation in the TonB box that disrupts the interaction between FhuE and TonB. See, Cadieux, N., Bradbeer, C. & Kadner, R. J. Sequence changes in the ton box region of BtuB affect its transport activities and interaction with TonB protein. J. Bacteriol. 182, 5954-5961 (2000); Funahashi, T. et al. Identification and characterization of an outer membrane receptor gene in *Acinetobacter baumannii* required for utilization of desferricoprogen, rhodotorulic acid, and desferrioxamine B as xenosiderophores. Biol. Pharm. Bull. 35, 753-760 (2012); the content of each of which is incorporated herein by reference.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method of treating *A. baumannii* infection, the method comprising: administering to a patient a composition comprising rifabutin at a dose sufficient for activation of a ferric-coprogen (FhuE) receptor of *A. baumannii* cells, to thereby facilitate entry of said rifabutin into said *A. baumannii* cells,
   wherein the composition is administered intravenously, by inhalation, or by modified release oral drug delivery system.

2. The method of claim 1, wherein the composition is administered intravenously.

3. The method of claim 2, wherein the dose provides an AUC and $C_{max}$ associated with activation of the FhuE receptor.

4. The method of claim 3, wherein the $C_{max}$ is greater than about 2 mg/L.

5. The method of claim 3, wherein said $C_{max}$ is greater than about 2 mg/L and less than about 50 mg/L.

6. The method of claim 3, wherein $C_{max}$>2 mg/L but <50 mg/L and AUC>10 mg*h/L and <300 mg*h/L.

7. The method of claim 1, wherein rifabutin is administered by inhalation.

8. The method of claim 1, wherein rifabutin is administered by a modified release oral drug delivery system.

9. The method of claim 1, wherein the composition comprising rifabutin includes the rifabutin, water, a solvent, and an acid.

10. The method of claim 9, wherein the composition is delivered intravenously at a rifabutin dose that is at least about 2 mg/kg q24 h, 1 mg/kg q12h, or 0.5 mg/kg q6 h.

11. The method of claim 9, wherein the solvent is selected from the group consisting of polyoxyethylene sorbitan monooleate (Tween 80), sorbitan monooleate polyoxyethylene sorbitan monolaurate (Tween 20), polyethylene glycol (PEG), propylene glycol, N-methyl-2-pyrrolidone (NMP), glycerin, ethanol, dimethylacetamide (DMA), diethylene glycol monoethyl ether (transcutol HP), and dimethyl isosorbide (DMI).

12. The method of claim 9, wherein the composition comprises about 2:1 solvent:rifabutin.

13. The method of claim 9, further comprising delivering the formulation to the patient by intravenous injection.

14. The method of claim 13, wherein the formulation is delivered at a dose that results in a $C_{max}$ is that is at least about 2 mg/L.

15. The method of claim 13, wherein the formulation is delivered at a dose that results in: 2 mg/L<$C_{max}$<50 mg/L; and 10 mg*h/L<AUC<300 mg*h/L.

16. The method of claim 13, wherein the formulation is delivered at a dose that is at least about 2 mg/kg q24 h, 1 mg/kg q12h, or 0.5 mg/kg q6 h.

17. A composition for use in treating *A. baumannii* infection, the composition comprising rifabutin, water, a solvent, and an acid in a liquid formulation.

18. The composition of claim 17, wherein the solvent is selected from the group consisting of polyoxyethylene sorbitan monooleate (Tween 80), sorbitan monooleate polyoxyethylene sorbitan monolaurate (Tween 20), polyethylene glycol (PEG), propylene glycol, N-methyl-2-pyrrolidone (NMP), glycerin, ethanol, dimethylacetamide (DMA), diethylene glycol monoethyl ether (transcutol HP), and dimethyl isosorbide (DMI).

19. The composition of claim 17, wherein the composition comprises about 2:1 solvent:rifabutin.

20. The composition of claim 17, wherein the composition is provided as an aqueous solution for intravenous delivery.

21. The composition of claim 17, wherein the composition is provided for a patient identified as infected with *A. baumannii*, and the composition includes rifabutin for IV delivery at a dosage that is at least about 2 mg/kg q24 h, 1 mg/kg q12h, or 0.5 mg/kg q6 h.

* * * * *